United States Patent [19]

Ozawa et al.

[11] Patent Number: 4,540,706
[45] Date of Patent: * Sep. 10, 1985

[54] INSECTICIDAL 1-N-PHENYLCARBAMOYL-3-(4-DIFLUOROMETHOXYPHENYL)-4-PHENYL-2-PYRAZOLINE DERIVATIVES

[75] Inventors: Kiyomi Ozawa; Yasuyuki Nakajima; Makoto Tsugeno; Shigeru Ishii; Masataka Hatanaka, all of Funabashi; Masayoshi Hirose; Masaki Kudo, both of Shiraoka, all of Japan

[73] Assignee: Nissan Chemical Industries Ltd., Tokyo, Japan

[*] Notice: The portion of the term of this patent subsequent to Aug. 7, 2001 has been disclaimed.

[21] Appl. No.: 461,666

[22] Filed: Jan. 27, 1983

Related U.S. Application Data

[63] Continuation-in-part of Ser. No. 455,735, Jan. 5, 1983, Pat. No. 4,464,386, and a continuation-in-part of Ser. No. 292,710, Aug. 13, 1981, Pat. No. 4,407,813.

[30] Foreign Application Priority Data

Feb. 5, 1982 [GB] United Kingdom ................. 8203354

[51] Int. Cl.³ .................... A01N 43/56; C07D 231/06
[52] U.S. Cl. ....................................... 514/403; 548/379
[58] Field of Search ..................... 548/379; 424/273 P

[56] References Cited

U.S. PATENT DOCUMENTS 4,070,365 1/1978 van Daalen et al. ................ 548/379
4,095,026 6/1978 Mulder et al. ...................... 548/379

FOREIGN PATENT DOCUMENTS 1108154 9/1981 Canada ........................... 424/273 P
WO79/00858 11/1979 PCT Int'l Appl. ............. 424/273 P Primary Examiner—Richard A. Schwartz
Assistant Examiner—Kurt G. Briscoe
Attorney, Agent, or Firm—Oblon, Fischer, Spivak, McClelland & Maier

[57] ABSTRACT

Pyrazoline derivatives useful as insecticides having the formula

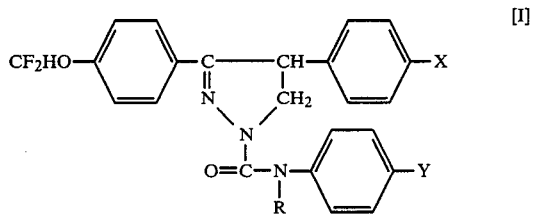

wherein X represents a hydrogen atom or a halogen atom; Y represents a halogen atom, a trifluoromethyl group or —A—R'; R represents a $C_{1-10}$ alkyl group, a lower alkenyl group or a lower alkynyl group; and A represents an oxygen atom, a sulfur atom, a sulfinyl group or a sulfonyl group and R' represents a halogen-substituted lower alkyl group.

13 Claims, No Drawings

INSECTICIDAL 1-N-PHENYLCARBAMOYL-3-(4-DIFLUOROMETHOXYPHENYL)-4-PHENYL-2-PYRAZOLINE DERIVATIVES

This application is a continuation in part of Ser. No. 455,735 filed on Jan. 5, 1983, now U.S. Pat. No. 4,464,386, and a continuation in part of Ser. No. 292,710 filed on Aug. 13, 1981, now U.S. Pat. No. 4,407,813.

The present invention relates to pyrazoline derivatives and an insecticide containing a pyrazoline derivative thereof as an active ingredient.

Various chemicals for insecticides have been studied and developed for a long time. These insecticides have been contributed for improvement of a productivity of agricultural crops. However, a development of a chemical having superior insecticidal activity has been required.

It has been known that 1-carbamoyl-2-pyrazoline derivatives are effective as insecticides in Japanese Unexamined Patent Publication No. 87028/1973, No. 41358/1976 and No. 87166/1977, etc. as pyrazoline derivatives.

It is an object of the present invention to provide insecticidal compounds which have excellent effects and low toxicity to mammals and fishes.

The foregoing object of the present invention has been attained by providing pyrazoline derivatives having the formula

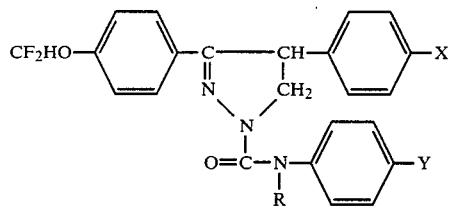

wherein X represents a hydrogen atom or a halogen atom; Y represents a halogen atom, a trifluoromethyl group or —A—R'; R represents a $C_{1-10}$ alkyl group, a lower alkenyl group or a lower alkynyl group; and A represents an oxygen atom, a sulfur atom, a sulfinyl group or a sulfonyl group and R' represents a halogen-substituted lower alkyl group.

The compounds of the present invention have been produced by the following reaction scheme.

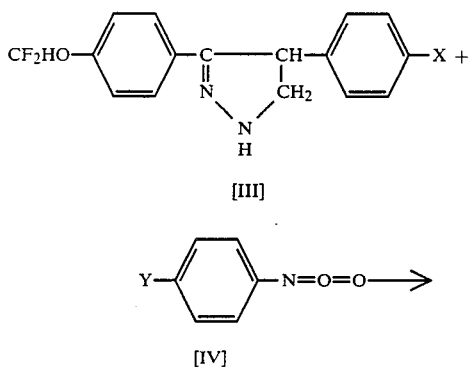

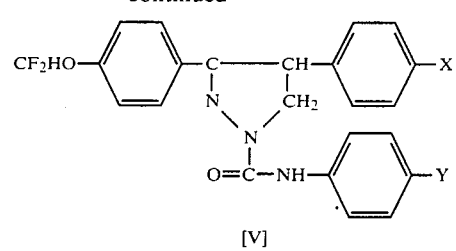

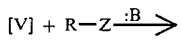

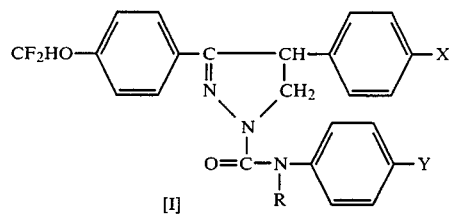

wherein X represents a hydrogen atom or a halogen atom; Y represents a halogen atom, a trifluoromethyl group or —A—R'; R represents a $C_{1-10}$ alkyl group, a lower alkenyl group or a lower alkynyl group; Z represents an iodine atom or a bromine atom; and A represents an oxygen atom, a sulfur atom, a sulfinyl group or a sulfonyl group and R' represents a halogen-substituted lower alkyl group.

The pyrazoline derivatives [V] can be produced by reacting 3-(4-difluoromethoxyphenyl)-2-pyrazoline derivative having the formula [III] with phenylisocyanate having the formula [IV] in the presence or absence of an inert solvent.

Suitable inert solvents include ethyl ether, benzene, toluene, acetonitrile, pyridine, dichloromethane, chloroform and carbon tetrachloride.

The reaction temperature and the reaction time can be selected depending upon the starting material. Usually, the reaction temperature is in a range of −20° C. to 100° C. The reaction time is preferably in a range of 0.5 to 24 hours.

The compounds having the formula [I] wherein A is SO or $SO_2$, can also be obtained by oxidizing the corresponding sulfide with an oxidizing agent such as hydrogen peroxide-acetic acid or meta chloroperbenzoic acid.

The pyrazoline derivatives [V] are alkylated with the compounds [VI] to obtain the compounds [I] of the present invention in the presence of a base.

Suitable bases include sodium hydride, potassium hydroxide and sodium hydroxide.

The reaction temperature and the reaction time can be selected depending upon the starting materials [V]. Usually, the reaction temperature is in a range of 0° C. to 80° C. The reaction time is preferably in a range of 0.5 to 24 hours.

The 3-(4-difluoromethoxyphenyl)-2-pyrazoline derivatives having the formula [III] as the starting material used in the reaction scheme are also insecticidal compounds which can be usually produced by the following reaction schemes.

Scheme 1:

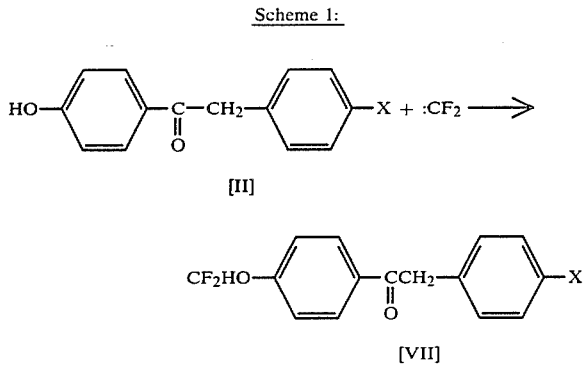

wherein X represents a hydrogen atom or a halogen atom.

Scheme 2:

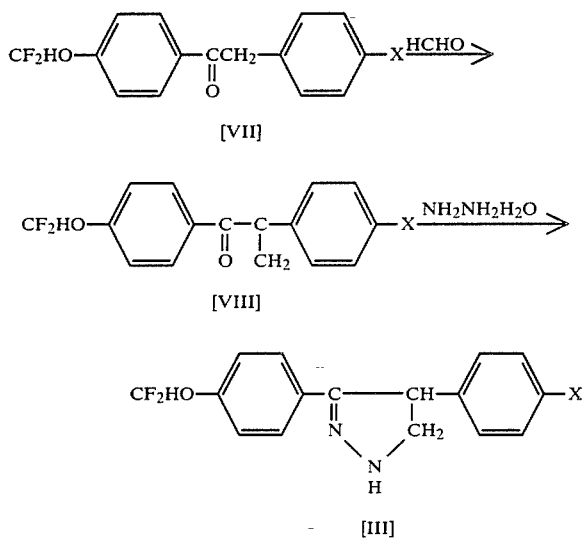

The 4-difluoromethoxy acylbenzene having the formula [VII] is produced by reacting 4-hydroxy acylbenzene having the formula [II] with difluorocarben.

The 2-pyrazoline derivative having the formula [III] is produced by reacting it with formaldehyde in an acidic medium in the presence of a solvent and a catalyst and reacting the product of the formula [VIII] with hydrazine in a solvent such as an alcohol such as ethanol and propanol.

The 2-pyrazoline derivatives having the formula [III] produced by these reactions can be isolated and purified. In many cases, however, these products are unstable to decompose by maintaining at room temperature. Thus, certain products should be maintained in nitrogen atmosphere at a low temperature. In a practical operation, the pyrazoline derivative having the formula [V] can be produced without an isolation and purification of the 2-pyrazoline derivative [III] by reacting the product with a phenyl isocyanate derivative.

The typical pyrazoline derivatives of the present invention will be described in Table 1.

TABLE 1

[Structure: CF$_2$HO—C$_6$H$_4$—C(=N)—CH(—C$_6$H$_4$—X)—CH$_2$—N(—C(=O)—N(R)—C$_6$H$_4$—Y)]

| No. | X | Y | R | Melting point (°C.) Refractive index |
|---|---|---|---|---|
| 1 | H | —Cl | —CH$_3$ | m.p. 103–107 |
| 2 | H | —Cl | —C$_2$H$_5$ | $N_D^{20}$ 1.5921 |
| 3 | H | —Cl | —n-C$_4$H$_9$ | $N_D^{20}$ 1.5855 |
| 4 | F | —Cl | —CH$_3$ | m.p. 116–118 |
| 5 | H | —Cl | —CH$_2$CH=CH$_2$ | $N_D^{20}$ 1.6023 |
| 6 | H | —Cl | —CH$_2$C≡CH | $N_D^{20}$ 1.6004 |
| 7 | Cl | —Cl | —CH$_3$ | |
| 8 | H | —CF$_3$ | —CH$_3$ | |
| 9 | H | —CF$_3$ | —C$_2$H$_5$ | |
| 10 | H | —CF$_3$ | —CH$_2$CH=CH$_2$ | |
| 11 | F | —CF$_3$ | —CH$_3$ | m.p. 143–145 |
| 12 | H | —OCF$_3$ | —CH$_3$ | m.p. 114–116 |
| 13 | H | —OCF$_3$ | —n-C$_3$H$_7$ | |
| 14 | F | —OCF$_3$ | —CH$_3$ | m.p. 140–142 |
| 15 | H | —OCF$_2$CF$_2$H | —CH$_3$ | m.p. 106–108 |
| 16 | H | —OCF$_2$CF$_2$H | —n-C$_3$H$_7$ | |
| 17 | H | —SCF$_3$ | —CH$_3$ | |
| 18 | H | —SCF$_3$ | —CH$_2$CH=CH$_2$ | |
| 19 | H | —Br | —CH$_3$ | |
| 20 | H | —Cl | —(CH$_2$)$_7$CH$_3$ | $N_D^{20}$ 1.5730 |
| 21 | H | —SOCF$_3$ | —CH$_3$ | |
| 22 | H | —SO$_2$CF$_3$ | —CH$_3$ | |

Certain compounds of the present invention include optical isomers having asymmetric carbon atom at 4-position of 2-pyrazoline ring. These isomers are also included in the compounds of the present invention.

The serial numbers of the compounds described in Table 1 are referred in the following Preparations, Compositions and Tests.

The compounds of the present invention are useful as insect pesticides for controlling insect pests in sanitation, and various insect pests in agriculture and horticulture which cause damages to rice, vegetable, fruits, cotton, and other crop plants and flowers and insect pests in forest and insect pests in storages.

The typical insect pests which are controlled by the compounds of the present invention are provided for purposes of illustration only.

Orthoptera
German Cockroach (*Blattella germanica*)
Rice Grasshopper (*Oxya yezoensis*)
Thysanoptera
Rice Thrips (*Baliothrips biformis*)
Hemiptera
Rice Stink Bug (*Lagynotomus elongatus*)
Green Stink Bug (*Nezera antennata*)
Rice Bug (*Leptocorisa chinensis*)
Bean Bug (*Riotortus clavatus*)
Cotton Bug (*Dysdercus cingulatus*)
Grape Leafhopper (*Epiacanthus stramineus*)
Green Rice Leafhopper (*Nephotettix cincticeps*)
Small Brown Planthopper (*Laodelphax striatellus*)
Brown Rice Planthopper (*Nilaparvata lugens*)
White-backed Rice Planthopper (*Sogatella furcifera*)
Citrus Psylla (*Diaphorina citri*)
Greenhouse Whitefly (*Trialeurodes vaporariorum*)
Cowpea Aphid (*Aphis craccivora*)
Cotton Aphid (*Aphis gossypii*)

-continued

| | |
|---|---|
| Apple Aphid | (*Aphis spiraecola*) |
| Green Peach Aphid | (*Myzue persicae*) |
| Citrus Mealybug | (*Planococcus citri*) |
| Comstock Mealybug | (*Pseudococcus censtocki*) |
| Red Scale | (*Aonidiella aurantri*) |
| San Jose Scale | (*Comstockaspis perniciosa*) |
| Arrowhead Scale | (*Unaspis yanonensis*) |
| Lepidoptera | |
| Apple Leafminer | (*Phyllonorycfer ringoneella*) |
| Citrus Leafminer | (*Phyllocnistis citrella*) |
| Diamondback Moth | (*Plutella xylostella*) |
| Pink Bollworm | (*Pectinophora gossypiella*) |
| Potato Tuberworm | (*Phthorimaea operculella*) |
| Peach Frut Moth | (*Carposina niponensis*) |
| Summer Fruit Tortrix | (*Adoxophyes orana*) |
| Oriental Fruit Moth | (*Grapholita molesta*) |
| Soybean Pod Borer | (*Leguminivora glycinivorella*) |
| Rice Stem Borer | (*Chilo suppressalis*) |
| Rice Leafroller | (*Chaphalocrocis medinalis*) |
| Pea Pod Borer | (*Etiella zinckenella*) |
| Oriental Corn Borer | (*Ostrinia furnacalis*) |
| Yellow Rice Borer | (*Tryporyza incertulas*) |
| Cutworm | (*Agrotis segetum*) |
| Cotton Looper | (*Anomis flava*) |
| American Bollworm Cotton Bollworm or Tabacco Budworm | (*Heliothis armigera, H. zea, H. virescens*) |
| Cabbage armyworm | (*Mamestra brassicae*) |
| Beet Semi Looper | (*Plusia nigrisigna*) |
| Rice Armyworm | (*Pseudaletia separata*) |
| Pink Borer | (*Sesamia inferens*) |
| Common Cutworm | (*Spodoptcra litura*) |
| Common White | (*Pieris rapae crucivora*) |
| Smaller Citrus Dog | (*Papilio xuthus*) |
| Rice Skipper | (*Parnara guttata*) |
| Coding Moth | (*Cydia pomonella*) |
| Coleoptera | |
| Cupreous Chafer | (*Anomala cuprea*) |
| Asiatic Garden Beetle | (*Maladera castanea*) |
| Japanese Beetle | (*Popillia Japonica*) |
| Twenty-eight-spotted Ladybeetle | (*Henosepilachna vigintioctopunctata*) |
| Cucurbit Leaf Beetle | (*Aulacophora femoralis*) |
| Rice Leaf Beetle | (*Oulema oryzae*) |
| Striped Flea Beetle | (*Phyllotreta striolata*) |
| Rice Plant Weevil | (*Echinocnemus squameus*) |
| Rice Water Weevil | (*Lissorhoptrus oryzophilus*) |
| Vegetable Weevil | (*Listroderes obliquus*) |
| Maize Weevil | (*Sitophilus zeamais*) |
| Bull Weevil | (*Anthonomus grandis*) |
| Corn Rootworms | (*Diabrotica spp.*) |
| Colorado Potato Beetle | (*Leptinotarsa decemlineata*) |
| Hymenoptera | |
| Fire Ant | (*Solenopsis geminata*) |
| Diptera | |
| Soybean Pud Gall Midge | (*Asphondylia spp.*) |
| Oriental Fruit Fly | (*Dacus dorsalis*) |
| Rice Leafminer | (*Hydrellia griseola*) |
| Rice Stem Maggot | (*Chlorops oryzae*) |
| Seedcorn Maggot | (*Hylemya platura*) |
| Mediterranean Fruit Fly | (*Ceratitis capitata*) |
| Rice Gall Midge | (*Orseolia oryzae*) |
| House Fly | (*Musca domestica*) |
| Pale House Mosquito | (*Culex pipiens pallens*) |
| Isoptera | |
| Termites | (*Coptotermes formosanus*) |

The insecticidal activity of the compounds of the present invention is imparted not only young larva but also old larva in direct or in penetration by direct contact or immersion. The compounds of the present invention are also effective to control various acarina and nematode.

In the application of the insecticidal composition of the present invention, it is preferable to apply it at a concentration of 0.01 to 10,000 ppm preferably 0.1 to 2,000 ppm of the active ingredient. In order to control aquatic insect pests, the composition having said concentration can be sprayed to the part to control the aquatic insect pests. Therefore, the concentration of the active ingredient in water can be lower.

In the application of the compound of the present invention as the insecticide, it is preferable to prepare a composition by mixing the active ingredient with a desired solid carrier such as clay, talc and bentonite; or a liquid carrier such as water, alcohols (methanol, ethanol etc.), ketones, ethers, aliphatic hydrocarbons, aromatic hydrocarbons (benzene, toluene, xylene etc.), esters and nitriles, if necessary, with an emulsifier, a dispersing agent, a suspending agent, a spreader, a penetrant and a stabilizer so as to form suitable compositions for practical applications in the form of an emulsifiable concentrate, an oil spray, a wettable powder, a dust, a granule, a tablet, a paste, a flowable, a bait poison, an aerosol, a fumigant, a mosquito-coil and mosquito mat.

It is possible to blend the active ingredient of the present invention to a suitable other active ingredient such as the other insecticides, germicides, herbicides, plant growth regulators, and fertilizers in the preparation of the composition or in the application.

The present invention will be further illustrated by certain examples of Preparations, Compositions and Tests which are provided for purposes of illustration only and are not intended to be limiting the present invention.

PREPARATION 1

1-[N-(4-chlorophenyl)-N-methyl-carbamoyl]-3-(4-difluoromethoxyphenyl)-4-phenyl-2-pyrazoline (Compound No. 1)

(a) Preparation of 3-(4-difluoromethoxyphenyl)-4-phenyl-2-pyrazoline (Intermediate)

A mixture of 17 g of benzyl-p-(hydroxy)phenyl ketone and 30 g of sodium hydroxide in 40 ml of water and 50 ml of dioxane was heated at 70° to 80° C. and 22 g of Freon 22 gas was fed into the solution during 1 hour while heating. After cooling the reaction mixture, 150 ml of water and 150 ml of ethyl ether were added to the reaction mixture and an organic phase was obtained by an extraction. The organic phase was separated and dried over anhydrous sodium sulfate and ethyl ether was distilled off to obtain 17.6 g of benzyl-p-(difluoromethoxy)phenyl ketone (melting point of 39.0°–40.0° C.). Into a mixture of 0.9 ml of piperidine, 0.9 ml of acetic acid, 25 ml of 37% formaline and 180 ml of methanol, 17.5 g of the resulting compound was added and the mixture was refluxed for 3 hours to react them. The reaction mixture was concentrated under a reduced pressure and 150 ml of water and 200 ml of chloroform were added. The resulting organic phase was separated and dried over anhydrous sodium sulfate and chloroform was distilled off to obtain 18.0 g of 4'-difluoromethoxy-2-phenylacrylophenone ($N_D^{20}$ 1.5819). A mixture of 17.5 g of the product, 8 ml of hydrazine hydrate and 150 ml of ethanol was refluxed for 3 hours to react them. After the reaction, the reaction mixture was concentrated under a reduced pressure and 80 ml of water and 100 ml of chloroform were added. The resulting organic phase was separated and dried over anhydrous sodium sulfate and chloroform was distilled off to obtain 17.5 g of 3-(4-difluoromethoxyphenyl)-4-phenyl-2-pyrazoline (melting point of 65°–75° C.).

(b) Preparation of
1-(4-chlorophenylcarbamoyl)-3-(4-difluoromethoxyphenyl)-4-phenyl-2-pyrazoline (Intermediate)

A mixture of 5.8 g of 3-(4-difluoromethoxyphenyl)-4-phenyl-2-pyrazoline obtained in the step (a) and 3.1 g of p-chlorophenyl isocyanate in 200 ml anhydrous ethyl ether was refluxed for 6 hours to react them. After cooling, the precipitated crystal (5.3 g) was separated by a filtration.

It was confirmed that the product was 1-(4-chlorophenylcarbamoyl)-3-(4-difluoromethoxyphenyl)-4-phenyl-2-pyrazoline (melting point of 147.0°-148.0° C.) by the NMR spectrum.

(c) Preparation of Compound No. 1

Into 40 ml of dimethylformamide, 5.5 g of 1-(4-chlorophenylcarbamoyl)-3-(4-difluoromethoxyphenyl)-4-phenyl-pyrazoline obtained in the step (b) was added. To the solution, 2.5 g of 50% potassium hydroxide and 3.0 g of methyliodide were added. The mixture was stirred for 3 hours at room temperature and was poured into 50 ml of water.

It was extracted twice with 50 ml of chloroform. The organic layer was washed with water and was dried over anhydrous sodium sulfate. The solvent was evaporated to obtain 5.0 g of the crude product. The crude product was purified by a silica gel column chromatography (benzene) and was recrystallized from n-hexane and ethyl ether (1:1) to obtain 3.2 g of the product. It was confirmed that the product was 1-[N-(4-chlorophenyl)-N-methylcarbamoyl]-3-(4-difluoromethoxyphenyl)-4-phenyl-2-pyrazoline (melting point of 103°-107° C.) by the NMR spectrum (Table 2).

PREPARATION 2-6

Compound No. 2, 3, 5, 6 and 20

These compounds were prepared according to Preparation 1 and those of NMR spectrums are also shown in Table 2.

PREPARATION 7 AND 8

Compound No. 12 and 15

In accordance with the process (a) and (b) of Preparation 1, 1-(4-trifluoromethoxyphenylcarbamoyl)-3-(4-difluoromethoxyphenyl)-4-phenyl-2-pyrazoline (melting point 125°-126° C.) and 1-(4-1',1',2',2'-tetrafluoroethoxyphenylcarbamoyl)-3-(4-difluoromethoxyphenyl)-4-phenyl-2-pyrazoline (melting point 132°-135° C.) were obtained as intermediates. Compounds Nos. 12 and 15 were prepared according to the process (c) of Preparation 1 using the above intermediate and NMR spectra thereof are shown in Table 2.

PREPARATION 9-11

Compound No. 4, 11 and 14

(a) Preparation of
3-(4-difluoromethoxyphenyl)-4-(4-fluorophenyl)-2-pyrazoline

In accordance with the process (a) of Preparation 1 except using 18.4 g of 4-fluorobenzyl-4'-(hydroxy)phenyl ketone instead of benzyl-p-(hydroxy)phenyl ketone, 4-fluorobenzyl-4'-(difluoromethoxy)phenyl ketone (melting point of 50°-56° C.) was obtained. Then, 4-difluoromethoxy-2-(4-fluorophenyl)acrylophenone ($N_D^{20}$ 1.5594) was produced by reacting formaline with the product.

Then, 15.2 g of 3-(4-difluoromethoxyphenyl)-4-(4-fluorophenyl)-2-pyrazoline was produced by reacting hydrazine hydrate with the product. The reaction mixture was used as a reagent in the following step (b) without any purification.

(b) Preparation of
1-(arylcarbamoyl)-3-(4-difluoromethoxyphenyl)-4-(4-fluorophenyl)-2-pyrazolines In accordance with the process (b) of Preparation 1, following 2-pyrazolines were obtained.
1-(4-Chlorophenylcarbamoyl)-3-(4-difluoromethoxyphenyl)-4-(4-fluorophenyl)-2-pyrazoline
(melting point 130°-133° C.)
1-(4-Trifluoromethylphenylcarbamoyl)-3-(4-difluoromethoxyphenyl)-4-(4-fluorophenyl)-2-pyrazoline
(melting point 158°-162° C.)
1-(4-Trifluoromethoxyphenylcarbamoyl)-3-(4-difluoromethoxyphenyl)-4-(4-fluorophenyl)-2-pyrazoline
(melting point 132°-134° C.)

(c) Preparation of Compound No. 4, 11 and 14

In accordance with the process (c) of Preparation 1, Compound No. 4, 11 and 14 were prepared and NMR spectra thereof are shown in Table 2.

TABLE 2

| Compounds | $^1$H-NMR spectra<br>δ (CDCl$_3$, TMS, ppm) |
|---|---|
| No. 1 | 3.39 (3H, s), 3.80–4.50 (3H, m), 6.40 (1H, t, J = 73Hz), 6.75–7.50 (13H, m) |
| No. 2 | 1.21 (3H, t, J = 7.0 Hz), 3.65–4.50 (5H, m), 6.37 (1H, t, J = 73 Hz), 6.75–7.50 (13H, m) |
| No. 3 | 0.85–1.85 (7H, m), 3.55–4.40 (5H, m), 6.38 (1H, t, J = 73 Hz), 6.75–7.50 (13H, m) |
| No. 4 | 3.38 (3H, s), 3.75–4.60 (3H, m), 6.39 (1H, t, J = 73 Hz), 6.75–7.50 (12H, m) |
| No. 5 | 3.80–4.50 (5H, m), 4.95–5.35 (2H, m), 5.65–6.30 (1H, m), 6.37 (1H, t, J = 73 Hz), 6.85–7.50 (13 H, m) |
| No. 6 | 2.22 (1H, t, J = 2.0 Hz), 3.80–4.45 (3H, m), 4.48 (2H, d, J = 2.0 Hz), 6.38 (1H, t, J = 73 Hz), 6.70–7.50 (13H, m) |
| No. 11 | 3.46 (3H, s), 3.80–4.65 (3H, m), 6.40 (1H, t, J = 73 Hz, 6.70–7.80 (12H, m) |
| No. 12 | 3.40 (3H, s), 3.85–4.60 (3H, m), 6.38 (1H, t, J = 73 Hz), 6.70–7.50 (13H, m) |
| No. 14 | 3.40 (3H, s), 3.80–4.60 (3H, m), 6.40 (1H, t, J = 73 Hz), 6.70–7.30 (12H, m) |
| No. 15 | 3.38 (3H, s), 3.80–4.60 (3H, m), 5.83 (1H, tt, J = 52 and 3 Hz), 6.32 (1H, t, J = 73 Hz), 6.60–7.35 (13H, m) |
| No. 20 | 0.80–1.80 (15H, m), 3.60–4.40 (5H, m), 6.36 (1H t, J = 73 Hz), 6.75–7.50 (13H, m) |

Certain examples of the compositions of the compounds of the present invention as insecticides are provided for purposes of illustration only and are not intended to be limiting the present invention.

| Composition 1: Emulsifiable concentrate: | |
|---|---|
| Active ingredient: | 10 wt. parts |
| Xylene | 80 wt. parts |
| Sorpol 2680 (Toho Chem.): | 10 wt. parts |

The components were uniformly mixed to prepare an emulsifiable concentrate. The emulsifiable concentrate was diluted with water to 50-100,000 times and it was sprayed in amounts of 10-500 liter/10 ares.

As the active ingredient, Compound No. 1, 2, 3, 4, 5, 6, 11, 12, 14 and 15 were used.

| Composition 2: Oil solution: | |
|---|---|
| Active ingredient: | 50 wt. parts |
| Methyl cellosolve: | 50 wt. parts |

The components were uniformly mixed to obtain an oily solution.

The oil solution was applied in amounts of 0.1 to 50 ml/m² to a drain or puddle or in amounts of 10-100 ml/10 ares by airplane spray. As the active ingredient, Compound No. 1, 2, 12 and other compounds in Table 1 were used.

| Composition 3: Wettable powder: | |
|---|---|
| Active ingredient: | 25 wt. parts |
| Zeeklite PFP: | 65 wt. parts |
| Carplex #80: | 2 wt. parts |
| Sorpol 5050: | 2 wt. parts |
| Sodium ligninesulfonate: | 6 wt. parts |

The components were uniformly ground and mixed to obtain a wettable powder. The wettable powder was diluted with 100 to 250,000 times of water and it was sprayed in amounts of 20 to 500 liter/10 ares.

As the active ingredient, Compound No. 1, 2, 12 and other compounds in Table 1 were used.

| Composition 4: Dust: | |
|---|---|
| Active ingredient: | 3.0 wt. parts |
| Carplex #80: | 0.5 wt. parts |
| Clay: | 95 wt. parts |
| Diisopropyl phosphate: | 1.5 wt. parts |

The components were uniformly mixed to obtain a dust. The dust was applied in amounts of 0.03 to 15 kg/10 ares.

As the active ingredient, Compound No. 1 and other compounds in Table 1 were used.

| Composition 5: Bait Poison: | |
|---|---|
| Wheat bran: | 52 wt. parts |
| Rice bran: | 15 wt. parts |
| Wheat powder: | 30 wt. parts |
| Raw sugar (muscovado): | 3 wt. parts |

The components were uniformly mixed and each active ingredient was added at a ratio of 0.2% base on the total components. Water was added at a ratio of 50% based on the total components and the mixture was granulated by a pelleter and dried at 50° to 60° C. by hot air. The resulting bait poison was placed in amounts of 0.1-5 g/m² around a root of a plant.

As the active ingredient, Compound No. 1 and other compounds in Table 1 were used.

The insecticidal activities of the compounds of the present invention will be illustrated by tests.

Experiment 1: Contact test for killing green rice leafhopper

Stems and leaves of a rice seedling were dipped in each emulsion of each composition of the active ingredient of the present invention (100 ppm) for 10 seconds and were dried in air. The stems and leaves were covered with a glass cylinder adult green rice leafhoppers which are resistant to the conventional organic phosphorus type insect pesticides were released into the glass cylinder which was covered with a cover having holes and was maintained in a constant temperature room at 25° C. Percent mortalities were measured at 48 hours or 120 hours after spraying.

The results are shown in Table 3.

TABLE 3

| Active ingredient | Percent mortality (%) | |
|---|---|---|
| | 48 hrs. | 120 hrs. |
| Compound No. 1 | 100 | — |
| Compound No. 2 | — | 100 |
| Compound No. 3 | — | 90 |
| Compound No. 4 | — | 100 |
| Compound No. 5 | — | 100 |
| Compound No. 6 | — | 100 |
| Compound No. 11 | — | 100 |
| Compound No. 12 | — | 100 |
| Compound No. 14 | — | 100 |
| Compound No. 15 | — | 100 |
| Reference Comp. A | 20 | 65 |

Note:
Reference Compound A:

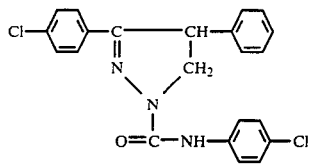

(Japanese Unexamined Patent Publication No. 41358/1976)

Experiment 2: Contact test for killing Common cutworm

Leaves of cabbage were dipped in each aqueous emulsion of each active ingredient of the compounds of the invention or the reference (1.25 ppm) for 10 seconds. The leaves were taken up and dried in air and put in a Petri dish. Common cutworms (second instar) were put in the Petri dish which was covered with a cover having many holes. The Petri dish was maintained in a constant temperature room at 25° C. for 48 hours and each percent mortality was determined. The results are shown in Table 4.

TABLE 4

| Active ingredient | Percent mortality (%) |
|---|---|
| Compound No. 1 | 100 |
| Compound No. 2 | 100 |
| Compound No. 4 | 100 |
| Compound No. 6 | 100 |
| Compound No. 11 | 100 |
| Compound No. 12 | 100 |
| Compound No. 14 | 100 |
| Compound No. 15 | 100 |
| Compound No. 20 | 100 |
| Reference Comp. A | 70 |

Note:
Reference Compound A:

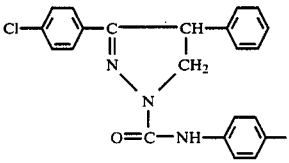

(Japanese Unexamined Patent Publication No. 41358/1976)

Experiment 3: Contact test for killing Twenty-eight-spotted Ladybeetle

Leaves of tomato were dipped in 1 ppm aqueous emulsion of each active ingredient of the compounds of the present invention and the reference for 10 seconds. The leaves were taken up and dried in air and put in a Petri dish. Ten of Twenty-eight-spotted Ladybeetles (second instar) were put in the Petri dish which was covered with a cover. The Petri dish was maintained in a constant temperature room at 25° C. for 48 hours and percent mortality was determined. The tests were carried out in two groups. The results are shown in Table 5.

TABLE 5

| Active ingredient | Percent mortality (%) |
| --- | --- |
| Compound No. 1 | 100 |
| Compound No. 2 | 100 |
| Compound No. 4 | 100 |
| Compound No. 5 | 100 |
| Compound No. 6 | 100 |
| Compound No. 11 | 100 |
| Compound No. 12 | 100 |
| Compound No. 14 | 100 |
| Compound No. 15 | 100 |
| Reference Comp. A | 70 |

Note:
Reference Compound A:

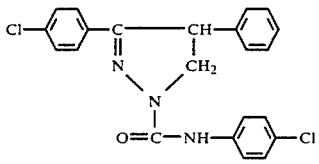

(Japanese Unexamined Patent Publication No. 41358/1976)

Experiment 4: Bait poison test for killing Common cutworm

Into each 1/5000 are pot, planting cabbage at 4 leaf stage, each bait poison composition 5 containing each active ingredient was put in an amount of 3 kg or 6 kg/10 ares. Common cutworm (fifth instar) were put in the pot. The pot was maintained in a constant temperature room at 25° C. After 5 hours, the percent mortality for each of the active ingredients was 100%.

We claim:

1. A pyrazoline derivative having the formula

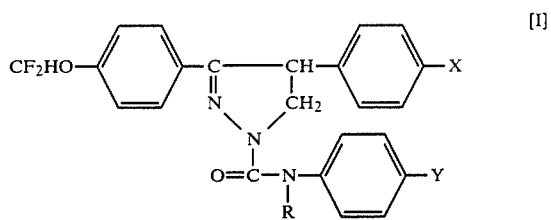

wherein X represents a hydrogen atom or a halogen atom; Y represents a halogen atom, a trifluoromethyl group or —A—R'; R represents a $C_1$-$C_{10}$ alkyl group, a lower alkenyl group or a lower alkynyl group; and A represents an oxygen atom, a sulfur atom, a sulfinyl group or a sulfonyl group and R' represents a halogen-substituted lower alkyl group.

2. The pyrazoline derivative according to claim 1 having the formula [I] wherein X represents a hydrogen atom or a fluorine atom; and A represents an oxygen atom or a sulfur atom.

3. The pyrazoline derivative according to claim 2 having the formula [I] wherein R represents an alkyl group of 1 to 10 carbon atoms, an allyl group or a propargyl group.

4. 1-[N-(4-chlorophenyl)-N-methylcarbamoyl]-3-(4-difluoromethoxyphenyl)-4-phenyl-2-pyrazoline according to claim 1.

5. 1-[N-(4-chlorophenyl)-N-ethylcarbamoyl]-3-(4-difluoromethoxyphenyl)-4-phenyl-2-pyrazoline according to claim 1.

6. 1-[N-(4-chlorophenyl)-N-methylcarbamoyl]-3-(4-difluoromethoxyphenyl)-4-(4-fluorophenyl)-2-pyrazoline according to claim 1.

7. 1-[N-(4-chlorophenyl)-N-allylcarbamoyl]-3-(4-difluoromethoxyphenyl)-4-phenyl-2-pyrazoline according to claim 1.

8. 1-[N-(4-chlorophenyl)-N-propargylcarbamoyl]-3-(4-difluoromethoxyphenyl)-4-phenyl-2-pyrazoline according to claim 1.

9. 1-[N-(4-trifluoromethylphenyl)-N-methylcarbamoyl]-3-(4-difluoromethoxyphenyl)-4-(4-fluorophenyl)-2-pyrazoline according to claim 1.

10. 1-[N-(4-trifluoromethoxyphenyl)-N-methylcarbamoyl]-3-(4-difluoromethoxyphenyl)-4-phenyl-2-pyrazoline according to claim 1.

11. 1-[N-(4-trifluoromethoxyphenyl)-N-methylcarbamoyl]-3-(4-difluoromethoxyphenyl)-4-(4-fluorophenyl)-2-pyrazoline according to claim 1.

12. 1-[N-(4-1',1',2',2'-tetrafluoroethoxyphenyl)-N-methylcarbamoyl]-3-(4-difluoromethoxyphenyl)-4-phenyl-2-pyrazoline according to claim 1.

13. An insecticidal composition which comprises a carrier and an insecticidally effective amount of a pyrazoline derivative defined in claim 1 as an active ingredient.

* * * * *

UNITED STATES PATENT AND TRADEMARK OFFICE
CERTIFICATE OF CORRECTION

PATENT NO. : 4,540,706

DATED : September 10, 1985

INVENTOR(S) : Kiyomi Ozawa et al

It is certified that error appears in the above-identified patent and that said Letters Patent is hereby corrected as shown below:

At column 1, last line, structure [IV], change " N=O=O " to -- N=C=O --.

At column 2, line 5, structure [V], change "$\overset{C}{\underset{N}{|}}$" to --$\overset{C}{\underset{N}{\|}}$--.

At column 3, line 33, structure [VIII], change "$\overset{C}{\underset{CH_2}{|}}$" to --$\overset{C}{\underset{CH_2}{\|}}$--.

At column 7, line 67, change "4" to --4'--.

Signed and Sealed this

Seventh Day of January 1986

[SEAL]

Attest:

DONALD J. QUIGG

Attesting Officer  Commissioner of Patents and Trademarks